United States Patent [19]

Goto et al.

[11] Patent Number: 4,936,121
[45] Date of Patent: Jun. 26, 1990

[54] CONDENSED HETEROCYCLIC COMPOUNDS, A PROCESS FOR PREPARING THE SAME AND A HERBICIDAL COMPOSITION THEREOF

[75] Inventors: Yukihisa Goto; Hiroshi Yagihara, both of Himeji; Kazuhisa Masamoto, Arai; Yasuo Morishima, Kobe; Yukihiro Sagawa, Arai; Hirokazu Osabe, Himeji, all of Japan

[73] Assignee: Daicel Chemical Industries Ltd., Osaka, Japan

[21] Appl. No.: 256,487

[22] Filed: Oct. 12, 1988

[30] Foreign Application Priority Data

Oct. 16, 1987 [JP] Japan .................. 62-262334

[51] Int. Cl.$^5$ .................. A01N 43/40; C07D 223/14; C07D 221/02
[52] U.S. Cl. ............................ 71/82; 71/92; 546/138; 546/183; 540/593
[58] Field of Search ............ 546/138, 183; 540/593; 71/82, 92

[56] References Cited

PUBLICATIONS

Kato et al, Yakugaku Zasshi 87(8) 961–966, 1967 Chem. Abs. vol. 68, 1968, Abs. 49422g.

Primary Examiner—Anton H. Sutto
Assistant Examiner—E. C. Ward
Attorney, Agent, or Firm—Bryan, Cave, McPheeters & McRoberts

[57] ABSTRACT

A compound of the formula (I)

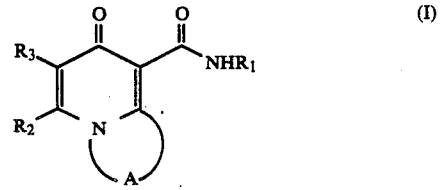

where A is an alkylene or alkenylene group, $R_1$ is an aryl group which may be substituted, $R_2$ is a hydrogen atom, a lower alkyl group, a lower alkenyl group, a lower alkynyl group, a halogenated lower alkyl group, a cycloalkyl group, a lower alkoxyalkyl group, a lower alkylthioalkyl group, a phenyl group which may be substituted or an aralkyl group which may be substituted, $R_3$ is a hydrogen atom, a halogen atom, a lower alkyl group, a lower alkenyl group, a lower alkynyl group or a halogenated lower alkyl group, or $R_2$ and $R_3$ may be combined to form a group of —$(CH_2)_n$—(n is 3 or 4), or salt thereof, which is useful as a herbicide.

13 Claims, No Drawings

CONDENSED HETEROCYCLIC COMPOUNDS, A PROCESS FOR PREPARING THE SAME AND A HERBICIDAL COMPOSITION THEREOF

BACKGROUND OF THE INVENTION

This invention relates to new condensed heterocyclic compounds, a process for preparing the same and a herbicidal composition thereof.

ART

4-Methyl-2-oxo-2H-quinolizine-1-carboxamide and 6,7,8,9-tetrahydro-4-methyl-2-oxo-2H-quinolizine-1-carboxamide are known as the heterocyclic compounds containing only one nitrogen atom as hetero atom which are condensed with a pyridone ring having a carbamoyl group at it's 3rd position, whose condensation side is between the 1st and 2nd positions of the pyridone ring, sharing its nitrogen atom [see Yakugakuzasshi, Vol. 87, p. 961 (1967)]. However, such condensed heterocyclic compounds as the compounds (I) of this invention mentioned below are not reported and their herbicidal activities are also not suggested or disclosed.

SUMMARY OF THE INVENTION

This invention provides a compound shown by the following formula (I) or salt thereof, and also a process for preparing the same and a herbicidal composition thereof.

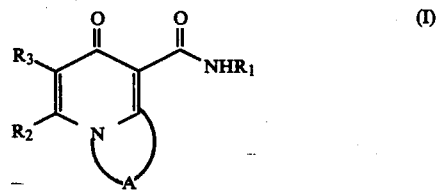

In the formula, A is a straight or branched chain alkylene group having 2 to 10 carbon atoms or a straight or branched chain alkenylene group having 2 to 10 carbon atoms; $R_1$ is an aryl group which may be substituted by one to five of a halogen, a cyano, a nitro, a lower alkyl, a phenyl, a halogenated lower alkyl, a lower alkoxy, a lower alkenyloxy, a lower alkynyloxy or a lower alkoxycarbonyl; $R_2$ is hydrogen atom, a lower alkyl group, a lower alkenyl group, a lower alkynyl group, a halogenated lower alkyl group, a cycloalkyl group, a lower alkoxyalkyl group, a lower alkylthioalkyl group, a phenyl group which may be substituted, by one to five of a halogen, a cyano, a nitro, a lower alkyl, a lower alkoxy or a halogenated lower alkyl or an aralkyl group which may be substituted by one to two of a halogen, a lower alkyl or a lower alkoxy a $R_3$ is a hydrogen atom, a halogen atom, a lower alkyl group, a lower alkenyl group, a lower alkynyl group or a halogenated lower alkyl group; or $R_2$ and $R_3$ may be combined to form a ring of $-(CH_2)_n-$ (n is 3 or 4).

In the formula (I), examples of the straight or branched chain alkylene or alkenylene groups having 2-10 carbon atoms in the definition of A are $-(CH_2)_3-$, $-(CH_2)_4-$, $-(CH_2)_5-$, $-CH(CH_3)CH_2CH_2-$, $-CH_2CH(CH_3)CH_2-$, $-CH_2CH_2CH(CH_3)-$, $-CH_2CH_2CH(C_2H_5)-$, $-CH(CH_3)CH_2CH_2CH_2-$, $-CH_2CH(CH_3)CH_2CH_2-$, $-CH_2CH_2CH(CH_3)CH_2-$, $-CH_2CH_2CH_2CH(CH_3)-$, $-CH_2CH_2CH_2CH(C_2H_5)-$, $-CH(CH_3)CH_2CH_2CH_2CH_2-$, $-CH_2CH_2CH_2CH_2CH(CH_3)-$, $-CH_2CH_2CH_2CH_2CH(C_2H_5)-$, $-(CH_2)_6-$, $-(CH_2)_7-$, $-(CH_2)_8-$, $-(CH_2)_9-$, $-(CH_2)_{10}-$ and $-CH=CH-CH=CH_2-$ in which the left bond is to bind with the nitrogen atom.

Examples of the halogen atoms as used in the definitions of $R_1$, $R_2$ and $R_3$ are chlorine, bromine, iodine and fluorine atoms.

The term "lower" as used in the lower alkyl, halogenated lower alkyl, lower alkoxy, lower alkoxycarbonyl, lower alkoxyalkyl or lower alkylthioalkyl group means a group containing one to five carbon atoms.

Specifically, the lower alkyl group may be methyl, ethyl, propyl, isopropyl, butyl, isobutyl, pentyl or isopentyl. The halogenated alkyl group may be chloromethyl, bromomethyl, difluoromethyl or trifluoromethyl. The lower alkoxy group may be methoxy, ethoxy, propoxy, isopropoxy or butoxy. The lower alkoxycarbonyl group may be methoxycarbonyl, ethoxycarbonyl, propoxycarbonyl or butoxycarbonyl. The lower alkoxyalkyl group may be methoxymethyl, ethoxymethyl, propoxymethyl, butoxymethyl or ethoxyethyl. The lower alkylthioalkyl group may be methylthiomethyl, ethylthiomethyl, methylthioethyl or ethylthioethyl.

The term "lower" as used in the lower alkenyl, lower alkynyl, lower alkenyloxy and lower alkynyloxy group means a group containing two to six carbon atoms.

Specifically, the lower alkenyl or lower alkynyl group may be vinyl, allyl, isopropenyl, 2-butenyl, 1,3-butadienyl, 2-pentenyl, 1,4-pentadienyl, 1,6-heptadienyl, 1-hexenyl, ethynyl or 2-propynyl. The lower alkenyloxy or lower alkynyloxy group may be vinyloxy, allyloxy, isopropenyloxy, 2-butenyloxy, 1,3-butadienyloxy, 2-pentenyloxy, 1-hexenyloxy, ethynyloxy or 2-propynyloxy.

The aralkyl in the aralkyl group which may be substituted by one or two of a halogen, a lower alkyl or a lower alkoxy may be benzyl, phenethyl, 3-phenylpropyl or 4-phenylbutyl. The halogen, lower alkyl and lower alkoxy as the substituents may be the same ones as mentioned above.

The cycloalkyl group may be cyclopropyl, cyclopentyl or cyclohexyl.

The aryl in the aryl group which may be substituted by one to five substituents may be phenyl, 1-naphthyl, 5,6,7,8-tetrahydro-1-naphthyl, 9-anthryl, 1,2,3,4,5,6,7,8-octahydro-9-anthryl, 1,2,3,4-tetrahydro-9-anthryl, 4-indanyl or 1,2,3,4,5,6,7-hexahydro-4-s-indacenyl.

The compound of the formula (I) in the invention may be prepared by the following methods.

Method A

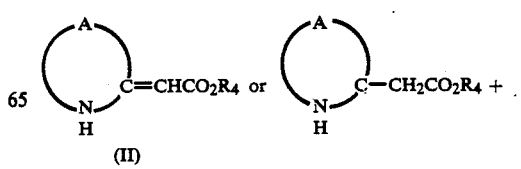

-continued
Method A

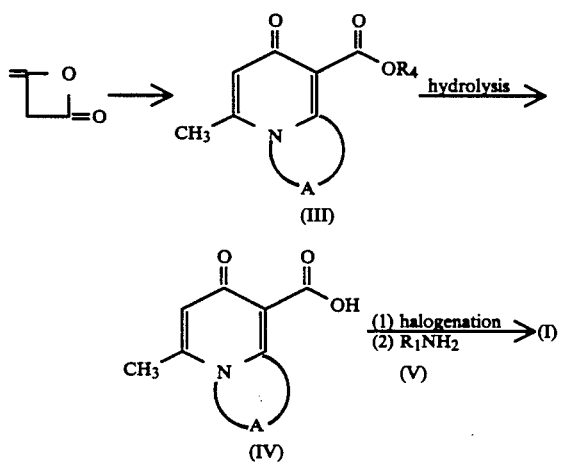

In the formulae (II), (III), (IV) and (V), A and $R_1$ have the same meanings as defined above, and $R_4$ is a lower alkyl group.

This method is carried out by reacting a compound of the formula (II) with diketene in the absence of any solvent or in an appropriate solvent such as benzene or toluene at a temperature of $-20°$ C. to $130°$ C. to obtain a compound of the formula (III), hydrolysing it by a conventional method, halogenating it with a halogenating agent such as thionyl chloride to give the acid halide and finally reacting the acid halide with an amine (V). The method is suitable to prepare a compound of the formula (I) wherein $R_2$ is methyl and $R_3$ is a hydrogen atom. Furthermore, the starting materials (II) can be easily prepared by conventional method.

Method B

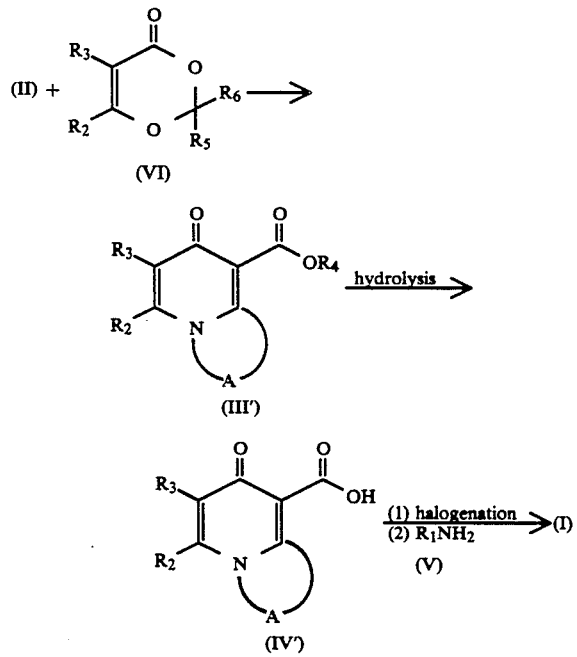

In the formulae (V), (III'), (IV') and (VI), A, $R_1$, $R_2$, $R_3$ and $R_4$ have the same meanings as defined above; $R_5$ and $R_6$ is a hydrogen atom, an alkyl group or phenyl group; and $R_5$ and $R_6$ together with the carbon atom to which they are bonded may form a cycloalkyl group.

This method is carried out by reacting a compound of the formula (II) with a compound of the formula (VI) in the absence of any solvent or in an appropriate solvent such as toluene, xylene or mesitylene while heating (e.g., at $100°-170°C$.) to obtain a compound of the formula (III') and then subjecting it to hydrolysis, halogenation and amidation in the same ways as those in Method A. The compounds of the formula (VI) can be obtained by a known method.

Method C

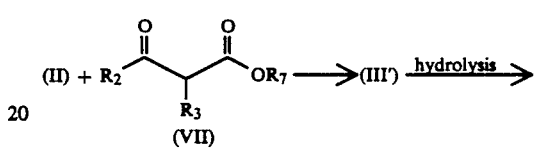

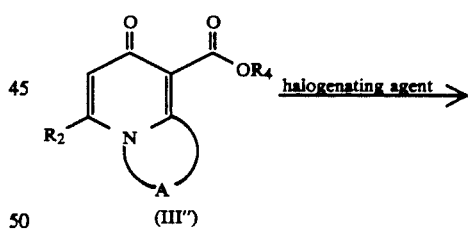

In the formulae (V) and (VII), $R_1$, $R_2$ and $R_3$ have the same meanings as defined above and $R_7$ is a lower alkyl group.

The method C is carried out by reacting a compound of the formula (II) with a compound of the formula (VII) in the presence of a molecular sieve in an inert solvent such as toluene, xylene or mesitylene while heating (e.g., at $100°-170°$ C.), and subjecting to hydrolysis, halogenation and amidation in the same ways as in Method A. The compounds of the formula (VII) can be obtained by a known method.

Method D

In the formulae (III'') and (V), A, $R_1$, $R_2$ and $R_4$ have the same meanings as defined above.

The method D is carried out by treating a compound of the formula (III'') with a halogenating agent such as bromine, chlorine or sulfuryl chloride, and then subjecting the resulting compound of the formula (III') to hydrolysis, halogenation and amidation in the same ways as those in Method B. The compound of the formula (III'') corresponds to that of the formula (III') wherein $R_3$ is a hydrogen atom. The method is suitable to prepare the compound of the formula (I) wherein $R_3$ is a halogen atom.

Method E

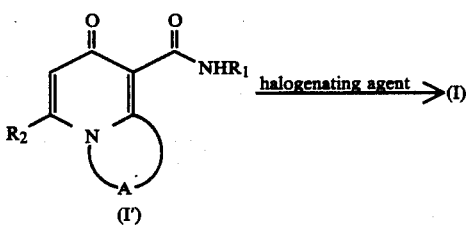

In the formula (I'), A, $R_1$ and $R_4$ have the same meanings as defined above.

This method reacts a compound of the formula (I') with a halogenating agent such as bromine, chlorine or sulfuryl chloride. The compound of the formula (I') corresponds to that of the formula (I) wherein $R_3$ is a hydrogen atom. It is suitable to prepare the compound of a formula wherein $R_3$ is a halogen atom.

The compound of the formula (I) according to the invention may form the salt with an inorganic acid such as hydrochloric acid, sulfuric acid or phosphoric acid; or an organic acid such as methanesulfonic acid, p-toluene sulfonic acid or trifluoroacetic acid. The salt is included in the invention. The salt can be obtained by treating the compound of the formula (I) with an acid in accordance with the conventional method.

The compounds (I) of this invention are useful as herbicides for paddy field, vegetable field (field farm), fruit gardens, meadows, lawns, woods and other fields of grass.

For herbicidal applications, the compounds of the present invention may be used as they are, but are generally formulated into herbicidal compositions such as wettable powders, granules or emulsifiable concentrates, in admixture with solid carriers, liquid carriers, surfactants and/or other adjuvants for preparations.

These compositions may preferably contain 10–80% for wettable powders, 0.1–20% for granules, or 10–50% for emulsifiable concentrates by weight of the active compound of this invention.

Examples of the solid carriers to be used for the compositions include fine powders or granules such as kaolinites, bentonites, clays, talcs, silicas, zeolite, pyrophilites, synthetic oxygen-containing silicones or calcium carbonate. Examples of the liquid carriers include aromatic hydrocarbons such as xylene or methylnaphthalene; alcohols such as ethanol, isopropanol, ethylene glycol or methylcellusolve; ketones such as acetone, isophorone or cyclohexanone; vegetable oils such as soya bean oil or cotton oil; or dimethylformamide, dimethylsulfoxide, acetonitrile or water.

Surfactants for dispersing or emulsifying are generally used with the liquid compositions. Their examples include nonionic types such as polyoxyethylene alkyl ethers, polyoxyethylene alkylaryl ethers, polyoxyethylene fatty acid esters, sorbitan fatty acid esters, polyoxyethylene sorbitan fatty acid esters or polyoxyethylene polyoxypropylene blockpolymer; or anionic types such as alkylsulfonates, alkylaryl sulfonates or polyloxyethylene alkylsulfates.

Examples of the adjuvants include lignine sulfates, arginates, polyacrylates, polyvinyl alcohol, vegetable gums, carboxymethycellulose (CMC) or hydroxyethylcellulose (HEC).

Also, the compounds of this invention can be, when needed, used in admixture with insecticides, acaricides, nematicides, bactericides, other herbicides, plant growth regulators, fertilizers or soil conditioners.

Dosage of the herbicidal compositions is generally 0.1–50 g by weight of the active compound, per acre, although it varies depending upon places, methods and kinds of plants.

In addition to the compounds shown by the following examples, interesting compounds which are included in the invention are specifically mentioned as:

3-chloro-N-(2,6-diethylphenyl)-6,7,8,9-tetrahydro-4-methyl-2-oxo-2H-quinolizine-1-carboxamide, N-(2,6-diethylphenyl)-1,2,3,4,6,7,8,9-octahydro-4-oxo-cyclopenta(c)quinolizine-5-carboxamide, 3-bromo-N-(4-bromo-2,6-diethylphenyl)-6,7,8,9-tetrahydro-4-methyl-2-oxo-2H-quinolizine-1-carboxamide, 3-bromo-N-(4-chloro-2,6-diethylphenyl)-6,7,8,9-tetrahydro-4-methyl-2-oxo-2H-quinolizine-1-carboxamide, 3-bromo-N-(2,6-diethyl-4-fluorophenyl)-6,7,8,9-tetrahydro-4-methyl-2-oxo-2H-quinolizine-1-carboxamide, 3-bromo-N-(2,6-diethyl-4-methylphenyl)-6,7,8,9-tetrahydro-4-methyl-2-oxo-2H-quinolizine-1-carboxamide, 3-bromo-N-(2,6-diethyl-4-methoxyphenyl)-6,7,8,9-tetrahydro-4-methyl-2-oxo-2H-quinolizine-1-carboxamide, 3-bromo-N-(4-cyano-2,6-diethylphenyl)-6,7,8,9-tetrahydro-4-methyl-2-oxo-2H-quinolizine-1-carboxamide, 3-bromo-N-(2,6-diethylphenyl)-4-trifluoromethyl-6,7,8,9-tetrahydro-2-oxo-2H-quinolizine-1-carboxamide, 3-bromo-4-ethyl-N-(2,6-diethylphenyl)-6,7,8,9-tetrahydro-2-oxo-2H-quinolizine-1-carboxamide, 3-bromo-6,7,8,9-tetrahydro-4-methyl-N-(2,3-dimethylphenyl)-2-oxo-2H-quinolizine-1-carboxamide, 3-bromo-N-(2-chlorophenyl)-6,7,8,9-tetrahydro-4-methyl-2-oxo-2H-quinolizine-1-carboxamide, 3-bromo-N-(2-ethyl-6-methoxyphenyl)-6,7,8,9-tetrahydro-4-methyl-2-oxo-2H-quinolizine-1-carboxamide, 6-bromo-N-(2,6-diethylphenyl)-1,2,3,7-tetrahydro-2,5-dimethyl-7-oxo-8-indolizinecarboxamide, 3-bromo-N-(2,6-diethylphenyl)-6,7,8,9-tetrahydro-4,9-dimethyl-2-oxo-2H-quinolizine-1-carboxamide, 3-bromo-N-(2,6-diethylphenyl)-6,7,8,9-tetrahydro-4,8-dimethyl-2-oxo-2H-quinolizine-1-carboxamide, 3-bromo-N-(2,6-diethylphenyl)-6,7,8,9,-tetrahydro-4,7-dimethyl-2-oxo-2H-quinolizine-1-carboxamide, 3-bromo-N-(2,6-diethylphenyl)-6,7,8,9-tetrahydro-4,6-dimethyl-2-oxo-2H-quinolizine-1-carboxamide, N-(2-biphenylyl)-3-bromo-2,6,7,8,9,10-hexahydro-4-methyl-2-oxo-pyrido[1,2-a]azepine-1-carboxamide, 3-bromo-2,6,7,8,9,10-hexahydro-4-methyl-2-oxo-N-[2-(1,1':3',1''-terphenyl)]-pyrido[1,2-a]azepine-1-carboxamide, N-(9-anthryl)-3-bromo-2,6,7,8,9,10-hexahydro-4-methyl-2-oxo-pyrido[1,2-a]azepine-1-carboxamide, N-(2,6-diethyl-4-fluorophenyl)-2,6,7,8,9,10-hexahydro-3,5-dimethyl-2-oxo-pyrido[1,2-a]azepine-1-carboxamide, 3-bromo-N-(2,6-diethyl-3-fluorophenyl)-2,6,7,8,9,10-hexahydro-4-methyl-2-oxo-pyrido[1,2-a]azepine-1-carboxamide, 3-bromo-N-(2,6-diethyl-4-trifluoromethylphenyl)-2,6,7,8,9,10-hexahydro-4-methyl-2-oxo-pyrido[1,2-a]azepine-1-carboxamide, 3-bromo-N-(5,7-dibromo-2,3-dihydro-1H-inden-4-yl)-2,6,7,8,9,10-hexahydro-4-methyl-2-oxo-pyrido[1,2-a]azepine-1-carboxamide, 3-bromo-N-(1,2,3,5,6,7-hexahydro-s-indacen-4-yl)-2,6,7,8,9,10-hexahydro-4-methyl-2-oxo-pyrido[1,2-a]azepine-1-carboxamide, 3-bromo-N-(5-ethyl-2,3-dihydro-1H-inden-4-yl)-2,6,7,8,9,10-hexahydro-4-methyl-2-oxo-pyrido[1,2-a]azepine-1-carboxamide, 3-bromo-N-(2,6-diethylphenyl)-6,7,8,9,10,11-hexahydro-4-methyl-2-oxo-2-H-pyrido[1,2-a]azocine-1-carboxamide and 3-bromo-N-(2,6-diethylphenyl)-2,6,7,8,9,10,11,12-octahydro-4-methyl-2-oxo-pyrido[1,2-a]azonine-1-carboxamide.

This invention is further illustrated by the examples.

EXAMPLE 1

N-(2,6-Diethylphenyl)-6,7,8,9-tetrahydro-4-methyl-2-oxo-2H-quinolizine-1-carboxamide (Compound 1)

A mixture of 3.10 g of methyl α-(hexahydro-2-pyridinylidene)acetate and 10 ml of xylene was gently refluxed, to which a solution of 7.81 g of 2-ethyl-2,6-dimethyl-4H-1,3-dioxin-4-one in 10 ml of xylene was dropwise added, taking 20 minutes. The mixture was further refluxed for 2 hours, removing the by-product a methyl ethyl ketone through Dean-Stark apparatus. The reaction mixture was cooled to room temperature. The resultant crystals were filtered, washed and dried under reduced pressure to obtain 4.11 g (Yield 93%) of methyl 6,7,8,9-tetrahydro-4-methyl-2-oxo-2H-quinolizine-1-carboxylate.

Mp.: 169°–171.5° C.

IR(KBr disc): 1637, 1725 cm$^{-1}$

NMR(CDCl$_3$) δ: 1.40–2.40 (m, 4H), 2.27 (s, 3H,), 2.77 (t, 2H), 3.80 (t, 2H), 3.80 (s, 3H), 6.17 (s, 1H).

A mixture of 3.50 g of methyl 6,7,8,9-tetrahydro-4-methyl-2-oxo-2H-quinolizine-1-carboxylate as obtained above and 126 g of 5% aqueous sodium hydroxide solution was stirred for 2 hours at 70° C. The reaction mixture was cooled to room temperature and added with 13.9 ml of concentrated hydrochloric acid under ice-cooling. The mixture was extracted with chloroform, and the extract was washed with saturated sodium chloride solution, dried and concentrated. The residue was recrystallized from a mixture of toluene and chloroform to afford 1.89 g (Yield 58%) of 6,7,8,9-tetrahydro-4-methyl-2-oxo-2H-quinolizine-1-carboxylic acid.

NMR(CDCl$_3$-DMSO-d$_6$) δ: 1.50–2.40 (m, 4H), 2.47 (s, 3H), 3.68 (t, 2H), 4.02 (t, 2H), 6.55 (s, 1H), 10.00–11.50 (br, 1H).

To a mixture of 1.00 g 6,7,8,9-tetrahydro-4-methyl-2-oxo-2H-quinolizine-1-carboxylic acid as obtained above and 15 ml of methylene chloride was dropwise added a mixture of 0.37 ml of SOCl$_2$ and 5 ml of methylene chloride taking 8 minutes under ice-cooling.

Then, a mixture of 0.79 g of 2,6-diethylaniline, 1.34 ml of triethylamine and 5 ml of methylene chloride was added to the above reaction mixture taking 7 minutes and stirring for an hour, while ice-cooling. After allowing to stand overnight at room temperature, the reaction mixture was washed with water and then saturated sodium chloride solution, dried and concentrated. The crystalline residue was recrystallized from ethyl acetate to afford 0.80 g (Yield 47%) of N-(2,6-diethylphenyl)-6,7,8,9-tetrahydro-4-methyl-2-oxo-2H-quinolizine-1-carboxamide.

Mp.: 134.5°–137° C.

EXAMPLE 2

3-Bromo-N-(2,6-diethylphenyl)-6,7,8,9-tetrahydro-4-methyl-2-oxo-2H-quinolizine-1-carboxamide (Compound 2)

A mixture of 0.11 ml of bromine and 8 ml of methylene chloride was dropwise added to a mixture of 0.70 g of N-(2,6-diethylphenyl)-6,7,8,9-tetrahydro-4-methyl-2-oxo-2H-quinolizine-1-carboxamide, 1.27 g of sodium carbonate and 12 ml of methylene chloride at room temperature taking 30 minutes and further stirred for 5 hours at room temperature. After filtering the insoluble material off, the solution was concentrated and the resulting crystalline residue was recrystallized from a mixture of ethyl acetate and methanol to afford 0.64 g (Yield 75%) of the title compound.

Mp.: 207.5°–210° C.

EXAMPLE 12

3-Bromo-N-(2,6-diethylphenyl)-2,6,7,8,9,10-hexahydro-4-methyl-2-oxo-pyrido[1,2-a]azepine-1-carboxamide (Compound 12)

A mixture of 20.0 g of methyl α-(hexahydro-2-azepinylidene)acetate and 77 ml of xylene was gently refluxed, to which a mixture of 41.9 g of 2,2,6-trimethyl-4H-1,3-dioxin-4-one and 41 ml of xylene was dropwise added taking 45 minutes and refluxed for 2 hours, removing the by-product acetone through a Dean-Stark apparatus. The reaction mixture was cooled to room temperature. The resulting crystals were filtered, washed and dried to afford 21.4 g (Yield 77%) of methyl 2,6,7,8,9,10-hexahydro-4-methyl-2-oxo-pyrido[1,2-a]azepine-1-carboxylate.

Mp.: 174°–176° C.

IR(KBr disc): 1628, 1722 cm$^{-1}$.

NMR(CDCl$_3$) δ: 1.40–2.00 (m, 6H), 2.28 (s, 3H), 2.47–2.97 (m, 2H), 3.83 (s, 3H), 3.70–4.20 (m, 2H), 6.09 (s, 1H).

To a mixture of 14.1 g of the resultant compoound, 38.2 g of sodium carbonate and 178 ml of methylene chloride was added dropwise a mixture of 3.69 ml of bromine and 89 ml of methylene chloride at room temperature taking 30 minutes, followed by stirring for an hour and 20 minutes at room temperature. The reaction mixture was washed with 10% aqueous sodium bisulfite, saturated sodium bicarbonate and water in this order, dried and concentrated. The crystalline residue was recrystallized from a mixture of ethyl acetate and methanol to afford 15.7 g (Yield 83%) of methyl 3-bromo-2,6,7,8,9,10-hexahydro-4-methyl-2-oxo-pyrido[1,2-a]azepine-1-carboxylate.

Mp.: 212°–213° C.

IR(KBr disc): 1580, 1620, 1728 cm$^{-1}$.

NMR(CDCl$_3$) δ: 1.43–2.10 (m, 6H), 2.62 (s, 3H), 2.47–2.97 (m, 2H), 3.83 (s, 3H), 3.90–4.30 (m, 2H).

A mixture of 15.5 g of the compound as obtained above and 98 g of 10% aqueous sodium hydroxide solution was stirred for 3 hours at 100° C. and cooled to room temperature, to which 21.6 ml of concentrated hydrochloric acid were added under ice-cooling. The precipitated crystals were filtered, washed and dried under reduced pressure to obtain 14.2 g (Yield 97%) of 3-bromo-2,6,7,8,9,10-hexahydro-4-methyl-2-oxo-pyrido[1,2-a]azepine-1-carboxylic acid.

Mp.: 234°–239° C.

IR(KBr disc): 1600, 1700 cm$^{-1}$.

A mixture of 0.23 ml of SOCl$_2$ and 4 ml of methylene chloride was dropwise added to a mixture of 0.90 g of the above mentioned carboxylic acid and 11 ml of methylene chloride taking 10 minutes and stirred for 5 hours under ice-cooling. Then, a mixture of 0.49 g of 2,6-diethylaniline, 0.61 g of triethylamine and 4 ml of methylene chloride was dropwise added to the above reaction mixture taking 10 minutes, followed by stirring for an hour and 40 minutes. After allowing to stand overnight, the reaction mixture was washed with 10% aqueous sodium hydroxide solution and water, dried and concentrated to obtain the crystalline residue. It was recrystallized from a mixture of ethyl acetate and methanol to afford 0.73 g (Yield 56%) of 3-bromo-N-(2,6-diethylphenyl)-2,6,7,8,9,10-hexahydro-4-methyl-2-oxo-pyrido 1,2-a azepine-1-carboxamide.

Mp.: 178°–179.5° C.

EXAMPLES 3–11 AND 13–38

In accordance with the method stated in "Method" of Table 1, Compounds 3–11 and 13–38 were prepared.

Tables 1 and 2 summarize the compound and their physical properties of said compounds.

TABLE 1

| Compound No. | R$_1$ | R$_2$ | R$_3$ | °A | Method | Mp. (°C.) |
|---|---|---|---|---|---|---|
| 1 | 2,6-diethylphenyl | CH$_3$ | H | —(CH$_2$)$_4$— | B | 134.5–137 |
| 2 | " | " | Br | " | E | 207.5–210 |
| 3 | " | " | H | —(CH$_2$)$_3$— | B | 149–151 |
| 4 | " | " | Br | " | E | 207–208.5 |
| 5 | " | " | H | —CH(CH$_3$)CH$_2$CH$_2$— | B | |
| 6 | " | " | Br | " | E | 211.5–213.5 |
| 7 | 3,5-diethyl-4-bromophenyl | CH$_3$ | Br | —CH(CH$_3$)CH$_2$CH$_2$— | E | 255.5–257 |
| 8 | 2,6-diethylphenyl | " | H | —CH$_2$CH$_2$CH(CH$_3$)— | B | 185–185.5 |
| 9 | 2,6-diethylphenyl | " | Br | " | E | 232–234.5 |
| 10 | 3,5-diethyl-4-bromophenyl | " | " | " | E | 272.5–273.5 |
| 11 | 2,6-diethylphenyl | " | H | —(CH$_2$)$_5$— | B | 149.5–150.5 |
| 12 | " | " | Br | " | D | 178–179.5 |

TABLE 1-continued

| Compound No. | R₁ | R₂ | R₃ | *A | Method | Mp. (°C.) |
|---|---|---|---|---|---|---|
| 13 | 2,6-diEt-phenyl | CH₃ | H | —CH=CH—CH=CH— | B | 214-216 |
| 14 | 2-Me-phenyl | " | " | " | B | 225-230 |
| 15 | 2,6-diEt-phenyl | " | CH₃ | —(CH₂)₅— | B | foam |
| 16 | " | " | " | —(CH₂)₄— | B | 171.5-173 |
| 17 | 4-Br-2,6-diEt-phenyl | " | Br | —(CH₂)₅— | D | 249.5-251.5 |
| 18 | 4-F-2,6-diEt-phenyl | " | " | " | D | 198-200 |
| 19 | 3,4-diBr-2,6-diEt-phenyl | CH₃ | Br | —(CH₂)₅— | D | 218.5-222 |
| 20 | 2-Br-6-Et-phenyl (Et,Et) | " | " | " | D | 171-173.5 |
| 21 | 2-F-3-Cl-5-O-i-Pr-phenyl | " | " | " | D | 213-216 |
| 22 | 4-OMe-2,6-diEt-phenyl | " | " | " | D | 207-209 |

TABLE 1-continued

| Compound No. | R₁ | R₂ | R₃ | *A | Method | Mp. (°C.) |
|---|---|---|---|---|---|---|
| 23 | 3,5-diethyl-4-methylphenyl (Et, Et, Me) | " | " | " | D | 240–242.5 |
| 24 | 2,6-dimethylphenyl (Me, Me) | " | " | " | D | 239–245.5 |
| 25 | 2-ethyl-6-methylphenyl (Et, Me) | CH₃ | Br | —(CH₂)₅— | D | 179.5–180 |
| 26 | 2-chloro-6-methylphenyl (Me, Cl) | " | " | " | D | 234.5–238 |
| 27 | phenyl | " | " | " | D | 218.5–220 |
| 28 | 2-chlorophenyl (Cl) | " | " | " | D | 252–255 |
| 29 | 2-methylphenyl (Me) | " | " | " | D | 219–221.5 |
| 30 | 2,6-dimethylphenyl (Me, Me) | " | " | " | D | 225–226.5 |
| 31 | naphthyl | CH₃ | Br | —(CH₂)₅— | D | 209–210.5 |

TABLE 1-continued

| Compound No. | R₁ | R₂ | R₃ | *A | Method | Mp. (°C.) |
|---|---|---|---|---|---|---|
| 32 | (5,6,7,8-tetrahydronaphthalen-1-yl) | " | " | " | D | 228–229 |
| 33 | 2,3-dichlorophenyl | " | " | " | D | 228–229 |
| 34 | 2,3-dibromophenyl | " | " | " | D | 207–212 |
| 35 | 2-Et, 3,5-dibromophenyl | " | " | " | D | 299–204.5 |
| 36 | (1,2,3,4,5,6,7,8-octahydroanthracen-9-yl) | " | " | " | D | 298–301 |
| 37 | (anthracen-1-yl) | CH₃ | Br | —(CH₂)₅— | D | 272.5–275 |
| 38 | (5,6,7,8-tetrahydronaphthalenyl with 2,3-diBr) | " | " | " | D | 244–249 |

*The bonding arm at left side is bound with the nitrogen atom

TABLE 2

| Example No. | IR ν-value (cm⁻¹) | Method | NMR Chemical shift δ value | Solvent |
|---|---|---|---|---|
| 1 | 1628, 1652 | KBr | 1.16(t,6H), 1.60–2.04(m,4H), 2.28(s,3H), 2.58(q,4H), 3.56(t,2H), 3.84(t,2H), 6.36(s,1H), 7.04(s,3H), 11.65(br,1H) | CDCl₃ |
| 2 | 1607, 1657 | " | 1.17(t,6H), 1.50–2.30(m,4H), 2.52(q,4H), 2.67(s,3H), 3.52(t,2H), 3.97(t,2H), 7.06(s,3H), 11.28(br,1H) | " |
| 3 | 1627, 1657 | " | 1.16(t,6H), 1.80–2.50(m,2H), 2.26(s,3H), 2.62(q,4H), 3.68(t,2H), 3.97(t,2H), 6.35(s,1H), 7.06(s,3H), 12.27(br,1H) | " |
| 4 | 1610, 1667 | " | 1.16(t,6H), 1.90–2.90(m,2H), 2.59(s,3H), 2.62(q,4H), 3.73(t,2H), 4.14(t,2H), 7.07(s,3H), 11.94(br,1H) | " |
| 5 | 1630, 1665 | " | | |
| 6 | 1603, 1663 | KBr | 1.16(t,6H), 1.38(d,3H), 1.60–2.60(m,2H), 2.61(q,4H), 2.66(s,3H), 3.00–4.40(m,2H), 4.40–5.00(m,1H), 7.07(s,3H), 11.96(br,1H) | CDCl₃ |
| 7 | 1608, 1663 | " | 1.15(t,6H), 1.40(d,3H), 1.60–2.60(m,2H), 2.61(q,4H), 2.66(s,3H), 3.00–4.40(m,2H), 4.40–5.00(m,1H), 7.18(s,2H), 12.00(br,1H) | " |
| 8 | 1635, 1665 | " | 1.16(t,6H), 1.29(d,3H), 1.60–2.50(m,2H), 2.30(s,3H), 2.61(q,4H), 3.80–4.30(m,2H), 4.30–5.00(m,1H), 6.37(s,1H), 7.05(s,3H), 12.35(br,1H) | " |
| 9 | 1610, 1663 | " | | |
| 10 | 1607, 1657 | " | | |
| 11 | 1630, 1655 | KBr | 1.19(t,6H), 1.50–2.17(m,6H), 2.35(s,3H), 2.66(q,4H), 3.37–3.80(m,2H), 3.90–4.37(m,2H), 6.35(s,1H), 7.07(s,3H), 11.48(br,1H) | CDCl₃ |
| 12 | 1600, 1662 | " | 1.18(t,6H), 1.75–2.10(m,6H), 2.67(q,4H), 2.70(s,3H), 3.30–3.70(m,2H), 4.00–4.20(m,2H), 7.08(s,3H), 10.58(br,1H) | " |
| 13 | 1642, 1660 | " | 1.19(t,6H), 2.62(s,3H), 2.68(q,4H), 6.67–8.10(m,7H), 9.60–9.93(m,1H), 12.45(br,1H) | " |
| 14 | 1650, 1670 | " | 2.56(s,3H), 6.53–8.00(m,9H), 9.53–9.86(m,1H), 13.37(br,1H) | " |
| 15 | 1622, 1660 | " | 1.18(t,6H), 1.43–2.10(m,6H), 2.13(s,3H), 2.33(s,3H), 2.66(q,4H), 3.27–3.73(m,2H), 3.87–4.33(m,2H), 7.04(s,3H), 11.50(br,1H) | " |
| 16 | 1625, 1660 | KBr | 1.17(t,6H), 1.43–2.10(m,4H), 2.17(s,3H), 2.37(s,3H), 2.64(q,4H), 3.57(t,2H), 3.91(t,2H), 7.06(s,3H), 12.00(br,1H) | CDCl₃ |
| 17 | 1602, 1665 | " | 1.16(t,6H), 1.50–2.13(m,6H), 2.61(q,4H), 2.70(s,3H), 3.30–3.73(m,2H), 4.03–4.43(m,2H), 7.18(s,2H), 10.92(br,1H) | " |
| 18 | 1600, 1660 | " | 1.16(t,6H), 1.50–2.13(m,6H), 2.63(q,4H), 2.68(s,3H), 3.27–3.70(m,2H), 4.03–4.43(m,2H), 6.74(d,2H), 10.73(br,1H) | " |
| 19 | 1610, 1655 | " | 1.11(t,3H), 1.14(t,3H), 1.50–2.20(m,6H), 2.56(q,2H), 2.70(s,3H), 2.89(q,2H), 3.27–3.73(m,2H), 4.00–4.50(m,2H), 7.35(s,1H), 11.23(br,1H) | " |
| 20 | 1610, 1655, 1665 | " | 1.12(t,3H), 1.15(t,3H), 1.50–2.17(m,6H), 2.59(q,2H), 2.69(s,3H), 2.82(q,2H), 3.30–3.80(m,2H), 4.00–4.43(m,2H), 6.91(d,1H), 7.36(d,1H), 11.06(br,1H) | " |
| 21 | 1595, 1667 | KBr | 1.34(d,6H), 1.60–2.30(m,6H), 2.73(s,3H), 3.27–3.90(m,2H), 4.10–4.80(m,3H), 7.10(d,1H), 8.09(d,1H), 12.20(br,1H) | CDCl₃—DMSO-d₆ |
| 22 | 1595, 1660 | " | 1.17(t,6H), 1.47–2.23(m,6H), 2.64(q,4H), 2.67(s,3H), 3.17–3.65(m,2H), 3.75(s,3H), 3.97–4.40(m,2H), 6.60(s,2H), 10.35(br,1H) | CDCl₃ |

TABLE 2-continued

| Example No. | IR v-value (cm$^{-1}$) | Method | NMR Chemical shift δ value | Solvent |
|---|---|---|---|---|
| 23 | 1600, 1665 | " | 1.16(t,6H), 1.47–2.17(m,6H), 2.28 (s,3H), 2.62(q,4H), 2.68(s,3H), 3.27–3.70(m,2H), 4.00–4.43(m,2H), 6.88(s,2H), 10.48(br,1H) | " |
| 24 | 1695, 1658 | " | 1.57–2.17(m,6H), 2.23(s,3H), 2.28 (s,3H), 2.71(s,3H), 3.10–3.60 (m,2H), 4.10–4.50(m,2H), 6.73–7.90(m,3H), 10.97(br,1H) | CDCl$_3$—DMSO-d$_6$ |
| 25 | 1610, 1660 | " | 1.18(t,3H), 1.47–2.13(m,6H), 2.28 (s,3H), 2.68(s,3H), 2.68(q,2H), 3.23–3.70(m,2H), 4.00–4.43(m,2H), 7.03(s,3H), 10.70(br,1H) | CDCl$_3$ |
| 26 | 1595, 1658 | KBr | 1.50–2.17(m,6H), 2.38(s,3H), 2.73 (s,3H), 3.07–3.57(m,2H), 4.13–4.53(m,2H), 7.00–8.00(m,3H), 11.14 (br,1H) | CDCl$_3$—DMSO-d$_6$ |
| 27 | 1600, 1612, 1663 | " | 1.50–2.20(m,6H), 2.64(s,3H), 3.20–3.63(m,2H), 3.93–4.36(m,2H), 6.70–7.80(m,5H), 11.88(br,1H) | CDCl$_3$ |
| 28 | 1585, 1670 | " | | |
| 29 | 1588, 1668 | " | 1.47–2.20(m,6H), 2.42(s,3H), 2.67 (s,3H), 3.30–3.80(m,2H), 3.93–4.40(m,2H), 6.77–7.37(m,3H), 7.80–8.13(m,1H), 11.72(br,1H) | CDCl$_3$ |
| 30 | 1600, 1660 | " | 1.50–2.20(m,6H), 2.28(s,6H), 2.67 (s,3H), 3.27–3.70(m,2H), 4.00–4.40(m,2H), 6.99(s,3H), 10.65 (br,1H) | " |
| 31 | 1595, 1657 | KBr | 1.30–2.15(m,6H), 2.53(s,3H), 3.20–3.70(m,2H), 3.76–4.20(m,2H), 7.07–8.50(m,7H), 12.54(br,1H) | CDCl$_3$ |
| 32 | 1597, 1658 | " | 1.30–2.20(m,10H), 2.20–3.00(m,4H), 2.64(s,3H), 3.20–3.73(m,2H), 3.90–4.36(m,2H), 6.60–7.30(m,2H), 7.67–7.93(m,1H), 11.50(br,1H) | " |
| 33 | 1597, 1660 | " | 1.43–2.30(m,6H), 2.66(s,3H), 3.27–3.80(m,2H), 4.00–4.50(m,2H), 7.00–7.30(m,2H), 8.03–8.55(m,1H), 12.47(br,1H) | " |
| 34 | 1603, 1668 | " | 1.43–2.20(m,6H), 2.68(s,3H), 3.30–3.90(m,2H), 4.00–4.50(m,2H), 6.70–7.70(m,3H), 12.00(br,1H) | " |
| 35 | 1602, 1670 | " | 1.17(t,3H), 1.47–2.20(m,6H), 2.70 (s,3H), 2.72(q,2H), 3.30–3.73 (m,2H), 4.06–4.47(m,2H), 7.32 (d,1H), 7.57(d,1H), 11.18(br,1H) | " |
| 36 | 1618, 1642 | KBr | 1.30–2.30(m,14H), 2.30–3.00(m,8H), 2.69(s,3H), 3.30–3.70(m,2H), 4.03–4.50(m,2H), 6.74(s,1H), 10.33 (br,1H) | CDCl$_3$ |
| 37 | 1597, 1672 | " | | |
| 38 | 1602, 1667 | " | 1.30–2.23(m,10H), 2.23–3.03(m,4H), 2.68(s,3H), 3.30–3.70(m,2H), 4.00–4.43(m,2H), 7.63(s,1H), 10.96(br,1H) | CDCl$_3$ |

TESTS

Growth-regulating activities on plants of the compounds of the invention were evaluated by the following method.

A carrier was prepared by mixing 50 parts (by weight) of talc, 25 parts of bentonite, 2 parts of Solpole-9047 (Toho Chemical Co., Ltd, Japan) and 3 parts of Solpole-5039 (Toho Chemical Co., Ltd, Japan). 50 parts of a test compound and 200 parts of the carrier were mixed to obtain a 20% wettable powder, followed by dispersing the powder in distilled water to make a dispersion of the defined concentrations.

Seeds of *Oryza sativa* L., *Echinochloa crus-galli* L., and *Raphanus sativus* L. were germinated in a laboratory dish, to which the dispersion was added. After breeding for 7 days in a thermostatic box kept at 25° C. under illumination of fluorescent tubes, growth of the plants was observed.

The results are shown in Table 3.

In the column of "Evaluation" of Table 3, the designation 1 denotes no influence, 2 denotes 25% growth inhibition, 3 denotes 50% growth inhibition, 4 denotes 75% growth inhibition and 5 denotes 100% growth inhibition.

TABLE 3

| Compound No. | Conc. (ppm) | Evaluation Plants | | |
|---|---|---|---|---|
| | | X | Y | Z |
| 1 | 20 | 2 | 3 | 5 |
| | 100 | 3 | 5 | 5 |
| 2 | 20 | 5 | 5 | 5 |
| | 100 | 5 | 5 | 5 |
| 4 | 20 | 4 | 5 | 5 |
| | 100 | 5 | 5 | 5 |

TABLE 3-continued

| Compound No. | Conc. (ppm) | Evaluation Plants | | |
|---|---|---|---|---|
| | | X | Y | Z |
| 6 | 20 | 5 | 5 | 1 |
|   | 100 | 5 | 5 | 2 |
| 7 | 20 | 5 | 5 | 4 |
|   | 100 | 5 | 5 | 5 |
| 8 | 20 | 1 | 1 | 4 |
|   | 100 | 3 | 3 | 5 |
| 9 | 20 | 4 | 4 | 5 |
|   | 100 | 5 | 5 | 5 |
| 10 | 20 | 4 | 5 | 5 |
|    | 100 | 5 | 5 | 5 |
| 11 | 20 | 3 | 5 | 4 |
|    | 100 | 5 | 5 | 5 |
| 12 | 20 | 5 | 5 | 5 |
|    | 100 | 5 | 5 | 5 |
| 13 | 20 | 1 | 3 | 5 |
|    | 100 | 3 | 5 | 5 |
| 14 | 20 | 1 | 1 | 1 |
|    | 100 | 2 | 2 | 2 |
| 15 | 20 | 5 | 5 | 5 |
|    | 100 | 5 | 5 | 5 |
| 16 | 20 | 3 | 4 | 5 |
|    | 100 | 5 | 5 | 5 |
| 17 | 20 | 5 | 5 | 5 |
|    | 100 | 5 | 5 | 5 |
| 18 | 20 | 5 | 5 | 5 |
|    | 100 | 5 | 5 | 5 |
| 19 | 20 | 5 | 5 | 5 |
|    | 100 | 5 | 5 | 5 |
| 20 | 20 | 5 | 5 | 5 |
|    | 100 | 5 | 5 | 5 |
| 21 | 20 | 1 | 4 | 5 |
|    | 100 | 3 | 5 | 5 |
| 22 | 20 | 5 | 5 | 5 |
|    | 100 | 5 | 5 | 5 |
| 23 | 20 | 5 | 5 | 5 |
|    | 100 | 5 | 5 | 5 |
| 24 | 20 | 5 | 5 | 5 |
|    | 100 | 5 | 5 | 5 |
| 25 | 20 | 4 | 5 | 5 |
|    | 100 | 5 | 5 | 5 |
| 26 | 20 | 5 | 5 | 5 |
|    | 100 | 5 | 5 | 5 |
| 27 | 20 | 3 | 1 | 5 |
|    | 100 | 3 | 3 | 5 |
| 28 | 20 | 3 | 4 | 4 |
|    | 100 | 4 | 5 | 5 |
| 29 | 20 | 5 | 5 | 5 |
|    | 100 | 5 | 5 | 5 |
| 30 | 20 | 5 | 5 | 5 |
|    | 100 | 5 | 5 | 5 |
| 31 | 20 | 5 | 5 | 5 |
|    | 100 | 5 | 5 | 5 |
| 32 | 20 | 5 | 5 | 5 |
|    | 100 | 5 | 5 | 5 |
| 33 | 20 | 4 | 5 | 5 |
|    | 100 | 5 | 5 | 5 |
| 34 | 20 | 5 | 5 | 5 |
|    | 100 | 5 | 5 | 5 |
| 34 | 20 | 5 | 5 | 5 |
|    | 100 | 5 | 5 | 5 |
| 35 | 20 | 5 | 5 | 5 |
|    | 100 | 5 | 5 | 5 |
| 36 | 20 | 5 | 5 | 5 |
|    | 100 | 5 | 5 | 5 |
| 37 | 20 | 5 | 5 | 5 |
|    | 100 | 5 | 5 | 5 |
| 38 | 20 | 5 | 5 | 5 |
|    | 100 | 5 | 5 | 5 |

X: *Oryza sativa L.*
Y: *Echinochloa crus-galli L.*

What we claim is:

1. A compound of the formula (1)

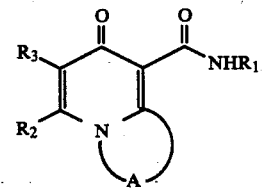

wherein A is straight or branched chain alkylene group having 2 to 10 carbon atoms; $R_1$ is an aryl group which may be substituted by one to four substituents of a halogen, a lower alkyl having 1 to 5 carbon atoms, a halogenated lower alkyl having 1 to 5 carbon atoms or a lower alkoxy group having 1 to 5 carbon atoms; $R_2$ is a a lower alkyl group having 1 to 5 carbon atoms; $R_3$ is a hydrogen atom, a halogen atom, or a lower alkyl group having 1 to 5 carbon atoms or salt thereof.

2. A compound of claim 1 in which A is a straight chain alkylene group having 4 or 5 carbon atoms.

3. A compound of claim 1 in which $R_1$ is 2,6-diethylphenyl, 2,6-diethyl-4-methylphenyl, 2,6-diethyl-4-methoxyphenyl, 2,6-diethyl-3 or 4-halophenyl, 2,6-diethyl-3,4-dihalophenyl, 2,3-dimethylphenyl, 2-ethyl-4,6-dihalophenyl, 2,4-dihalo-5,6,7,8-tetrahydro-1-naphthyl or 2-ethyl-6-methylphenyl group.

4. A compound of claim 1 in which $R_2$ is a methyl group.

5. A compound of claim 1 in which $R_3$ is a hydrogen atom, bromine atom or methyl group.

6. A compound of claim 1 which is N-(2,6-diethylphenyl)-6,7,8,9-tetrahydro-4-methyl-2-oxo-2H-quinolizine-1-carboxamide, 3-bromo-N-(2,6-diethylphenyl)-6,7,8,9-tetrahydro-4-methyl-2-oxo-2H-quinolizine-1-carboxamide, N-(2,6-diethylphenyl)-2,6,7,8,9,10-hexahydro-4-methyl-2-oxopyrido 1,2-a azepine-1-carboxamide 3-bromo-N-(2,6-diethylphenyl)-2,6,7,8,9,10-hexahydro-4-methyl-2-oxopyrido 1,2-a azepine-1-carboxamide, N-(2,6-diethylphneyl)-2,6,7,8,9,10-hexahydro-3,4-dimethyl-2-oxopyrido 1,2-a azepine-1-carboxamide, 3-bromo-N-(4-bromo-2,6-diethylphenyl)-2,6,7,8,9,10-hexahydro-4-methyl-2-oxo-pyrido[1,2-a]azepine-1-carboxamide, 3-bromo-N-(2,6-diethyl-4-fluorophenyl)-2,6,7,8,9,10-hexahydro-4-methyl-2-oxo-pyrido[1,2-a]azepine-1-carboxamide, 3-bromo-N-(3,4-dibromo-2,6-diethylphenyl)-2,6,7,8,9,10-hexahydro-4-methyl-2-oxo-pyrido[1,2-a]azepine-1-carboxamide, 3-bromo-N-(3-bromo-2,6-diethylphenyl)-2,6,7,8,9,10-hexahydro-4-methyl-2-oxo-pyrido[1,2-a]azepine-1-carboxamide, 3-bromo-N-(2,6-diethyl-4-methoxyphenyl)-2,6,7,8,9,10-hexahydro-4-methyl-2-oxo-pyrido[1,2-a]azepine-1-carboxamide, 3-bromo-N-(2,6-diethyl-4-methylphenyl)-2,6,7,8,9,10-hexahydro-4-methyl-2-oxo-pyrido[1,2-a]azepine-1-carboxamide, 3-bromo-N-(2,4-dibromo-6-ethylphenyl)-2,6,7,8,9,10-hexahydro-4-methyl-2-oxo-pyrido[1,2-a]azepine-1-carboxamide or 3-bromo-N-(2,4-dibromo-5,6,7,8-tetrahydro-1-naphthyl)-2,6,7,8,9,10-hexahydro-4-methyl-2-oxo-pyrido[1,2-a]-azepine-1-carboxamide.

7. A herbicidal composition which comprises at least one compound as claimed in claim 1 as the active ingredient and a carrier therefor.

8. A method of inhibiting the growth of plants which comprises treating said plants with an effective amount of a compound of claim 1.

9. A method of inhibiting the growth of plants wherein the plants are treated with an effective amount of a compound of claim 2.

10. A method of inhibiting the growth of plants wherein the plants are treated with an effective amount of a compound of claim 3.

11. A method of inhibiting the growth of plants wherein the plants are treated with an effective amount of a compound of claim 4.

12. A method of inhibiting the growth of plants wherein the plants are treated with an effective amount of a compound of claim 5.

13. A method of inhibiting the growth of plants wherein the plants are treated with an effective amount of a compound of claim 6.

* * * * *

UNITED STATES PATENT AND TRADEMARK OFFICE
CERTIFICATE OF CORRECTION

PATENT NO. : 4,936,121

DATED : June 26, 1990

INVENTOR(S) : YUKIHISA GOTO et al.

It is certified that error appears in the above-identified patent and that said Letters Patent is hereby corrected as shown below:

On the title page, in the ABSTRACT, line 2 (after formula): Change "where" to --wherein--.

Column 1, line 55: Change "alkoxy a" to --alkoxy;--.

Column 2, line 55: Change "1,2,3,4,5,6,7-hexahydro-4-s-indacenyl" to --1,2,3,5,6,7-hexahydro-4-s-indacenyl--.

Column 7, line 11: change "2-H" to --2H--.

Column 8, line 41: Change "compoound," to --compound,--.

Column 10, line 11: Delete "of said compounds".

Column 17, line 13: Change "3,97(t,2H), 6,35(s,1H)," to --3.97(t,2H), 6.35(s,1H),--.

Column 21, line 55-56: Delete the second occurrence of the following in Table 3:
"34     20     5     5     5
        100    5     5     5"

Column 21, line 66: On the line immediately below "Y: Echinochloa crus-galli L.", insert --Z: Raphanus sativus L.--.

In the claims,

Column 22, line 16: In claim 1, change "$R^2$ is a a lower" to --$R^2$ is a lower--.

UNITED STATES PATENT AND TRADEMARK OFFICE
CERTIFICATE OF CORRECTION

PATENT NO. : 4,936,121

DATED : June 26, 1990

INVENTOR(S) : YUKIHISA GOTO et al.

It is certified that error appears in the above-identified patent and that said Letters Patent is hereby corrected as shown below:

Column 22, line 42: In claim 6, change "diethylphneyl" to --diethylphenyl--.

Signed and Sealed this

Sixth Day of April, 1993

*Attest:*

STEPHEN G. KUNIN

*Attesting Officer*    Acting Commissioner of Patents and Trademarks